US00PP09730P

United States Patent [19]

Dümmen

[11] Patent Number: Plant 9,730

[45] Date of Patent: Dec. 3, 1996

[54] GERANIUM PLANT NAMED 'HWD SORPRESA'

[75] Inventor: Günter Dümmen, Rheinberg-Eversael, Germany

[73] Assignee: Dummen Jungpflanzenkulturen, Rheinberg-Eversael, Germany

[21] Appl. No.: 520,861

[22] Filed: Aug. 30, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Proprietary Rights International

[57] ABSTRACT

A new and distinct cultivar of Geranium plant named HWD Sorpresa, characterized by its semi-double rubine red flowers; large umbels; large flowers; numerous flowers per umbel; and dark green leaf color.

1 Drawing Sheet

The present invention relates to a new and distinct cultivar of Geranium plant, botanically known as *Pelargonium*× *hortorum*, known as the variety Duesor, and hereinafter referred to by the cultivar name HWD Sorpresa.

The new cultivar is a product of a planned breeding program conducted by the inverter in Rheinberg, Germany. The objective of the breeding program was to develop a new early-flowering, semi-double geranium with red purple-colored flowers.

The new cultivar originated from a cross made by the inventor of the nonpatented cultivar Dueaqua as the male or pollen parent with the patented cultivar Tango (U.S. Plant Pat. No. 5,933) as the female or seed parent.

The cultivar HWD Sorpresa was discovered and selected by the inventor as a flowering plant within the progeny of the stated cross in a controlled environment in Rheinberg, Germany. Asexual reproduction of the new cultivar by terminal cuttings taken at Rheinberg, Germany, has shown that the unique features of this new Geranium are stabilized and reproduced true to type in successive generations of asexual reproduction.

The following traits have been repeatedly observed and are determined to be the unique characteristics of HWD Sorpresa.These characteristics in combination distinguish HWD Sorpresa as a new and distinct cultivar:

1. Semi-double rubine red flowers.
2. Large umbels.
3. Large flowers.
4. Many flowers per umbel.
5. Dark green leaf color.

In comparison to the parent cultivar Dueaqua, plants of the new Geranium have darker foliage color, larger flowers and more purple flower color. In comparison to the parent cultivar Tango plants of the new Geranium have rubine red (not bright red) flower color and larger flowers.

The new Geranium is similar in petal color to the patented cultivar Designer Rose (U.S. Plant Pat. No. 8,524) and the cultivars HWD Fuega and HWD Violetta (disclosed in the inventor's pending applications). In comparison to the cultivar Designer Rose, plants of the new Geranium have larger umbels, more flowers per umbel and larger flowers. In comparison to the cultivars HWD Fuega and HWD Violetta, plants of the new Geranium have more flowers per umbel. Compared to the cultivar HWD Fuega, plants of the new Geranium have smaller umbels, lighter foliage color, larger plant size, but shorter peduncles. Compared to the cultivar HWD Violetta, plants of the new Geranium do not have a zonation pattern on the foliage.

The accompanying colored photograph illustrates the overall appearance of the new cultivar, showing the colors as true as it is reasonably possible to obtain in colored reproductions of this type. Flower color appears more red than the actual flower color due to light reflectance. The photograph comprises a top perspective view of a typical potted plant of HWD Sorpresa with one plant in a 10-cm container.

The cultivar HWD Sorpresa has not been observed under all possible environmental conditions. The phenotype may vary somewhat with variations in environment such as temperature and light intensity, without, however, any variance in genotype. The following observations, measurements and comparisons describe plants grown in Rheinberg, Germany, under commercial practice in a glass-covered greenhouse with day temperatures of 24° C. and night temperatures of 18° to 20° C. and light levels of 45,000 to 60,000 lux. Plants were grown in 10-cm pots with one plant per pot.

In the following descriptions color references are made to The Royal Horticultural Society Colour Chart except where general terms of ordinary dictionary significance are used.

Classification:

*Botanical.*—*Pelargonium*×*hortorum.*

*Commercial.*—Zonal Geranium.

*Cultivar.*—'HWD Sorpresa'.

Parentage:

*Male parent.*—Nonpatented cultivar Dueaqua.

*Female parent.*—Tango (U.S. Plant Pat. No. 5,933).

Propagation: Type cutting: Terminal cuttings. Time to initiate roots: Summer 27° C., 21 days; winter: 20° C., 28 days Plant description:

*General appearance.*—Rounded; compact plant size; upright; freely branching.

*Foliage description.*—Arrangement: Generally alternate. Shape: Orbicular with rounded tip and cordate base. Size: Length: 6.5 to 7.5 cm. Width: 6.5 to 9 cm. Texture: Velvety; pubescent on upper and under surfaces. Margin: Crenate. Color: Young foliage, upper surface: 137A. Young foliage, under surface: 137C. Mature foliage, upper surface: 137A. Mature foliage, under surface: 138B. Zonation pattern: None. Veins, upper surface: 143A. Veins, under surface: 143A. Petiole: 143A. Venation pattern: Palmate. Petiole: Length 7 cm. Diameter: 3 mm.

*Stem description: Internode length.*—1.5 to 2 cm. *Stem color.*—143A. *Lateral branch number.*—6 to 8. *Lateral branch length.*—10 to 13 cm.

Flowering description:

*Flowering habit.*—Freely flowering. Flowers arranged in umbels.

*Natural flowering season.*—Year-round.

*Flowers borne.*—Flower buds develop in apical leaf axis. Umbels are displayed above the foliage.

*Quantity of inflorescences.*—Usually 8 open umbels and at least 4 to 5 developing umbels per plant at one time.

*Umbels.*—Form: Rounded. Diameter: 12 cm. Depth (height): 8 to 9 cm.

*Flowers.*—Form: Semi-double. Shape: Rounded. Quantity of flowers per umbel: 39 to 50. Diameter: 5.5 cm. Depth (height): 1.5 cm.

*Petals.*—Shape: Obovate with rounded tip. Arrangement: Rosette, overlapping. Quantity: 6. Aspect: Flat. Size: Length: 2.5 cm. Width: 2 cm. Texture: Satiny, smooth. Margin: Entire. Color: When opening, upper surface: 57A. When opening, under surface: 58C. Upper surface: 57A. Under surface: 58C. Fading to, upper surface: No fading observed. Fading to, under surface: 69A at base.

*Petaloids.*—Shape: Irregular, generally obovate with rounded or clefted tip. Arrangement: Rosette, overlapping. Quantity: 4 to 6. Size: Length: 1 to 2 cm. Width: 0.5 to 1 cm. Texture: Satiny, smooth. Margin: Generally entire. Color: When opening, upper surface: 52A. When opening, under surface: 52B. Upper surface: 52A. Under surface: 52B. Fading to, upper surface: No fading observed. Fading to, under surface: 36D at base.

*Peduncle (umbel stem).*—Angle: Erect. Length: 11.5 cm. Pubescence: Very fine. Color: 137C.

*Pedicel (individual flower stem).*—Angle: Erect, rigid. Length: 3 cm. Pubescence: Very fine. Color: 183A.

*Flower bud.*—Shape: Ovoid. Length: 1.3 cm. Diameter: 5 to 7 mm. Color 57A.

*Sepals.*—Arrangement: Rosette. Quantity: 5. Size: Length 1.1 cm. Width: 2.5 mm. Shape: Acuminate with apiculate tip. Texture: Velvety. Margin: Entire. Color: Upper surface: 184B at base fading to 139C at tip. Under surface: 184A at base fading to 139C at tip.

*Reproductive organs.*—Androecium: Stamen number 8. Anther size: 2 mm. Anther color: 180C. Pollen color: 172B. Gynoecium: Pistil number: 1. Pistil length: 1 cm. Stigma shape: Decurrent. Stigma color: 61B. Style length: 5 mm. Style color: 61B.

*Ploidy level.*—Tetraploid.

Disease resistance: No fungal, bacterial nor viral problems observed.

Seed development: Seed production is very rarely observed.

It is claimed:

1. A new and distinct cultivar of Geranium plant named HWD Sorpresa, as illustrated and described.

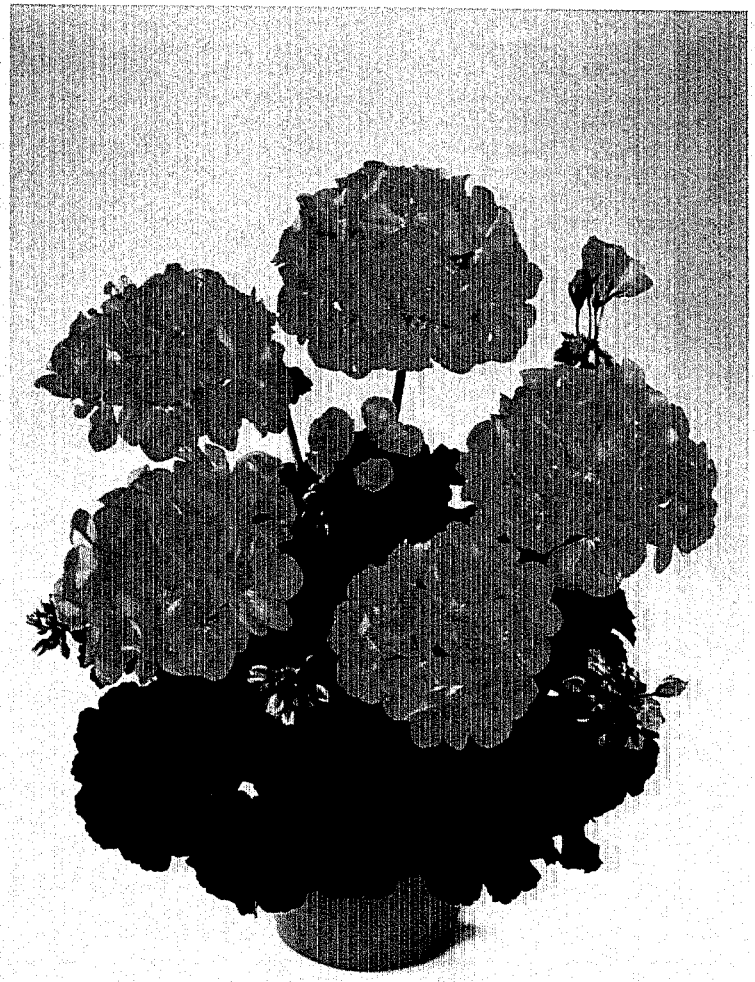

* * * * *